United States Patent [19]

Smart

[11] Patent Number: 5,379,645
[45] Date of Patent: Jan. 10, 1995

[54] TEST CELL FOR APPLYING DIRECTIONALLY VARIABLE THREE DIMENSIONAL STRESS FIELDS TO A TEST SPECIMEN

[75] Inventor: Brian G. D. Smart, Falkirk, United Kingdom

[73] Assignee: Heriot-Watt University, Scotland, United Kingdom

[21] Appl. No.: 90,153

[22] PCT Filed: Jan. 30, 1992

[86] PCT No.: PCT/GB92/00172
§ 371 Date: Jul. 23, 1993
§ 102(e) Date: Jul. 23, 1993

[87] PCT Pub. No.: WO92/14131
PCT Pub. Date: Aug. 20, 1992

[30] Foreign Application Priority Data

Feb. 1, 1991 [GB] United Kingdom ............... 9102248

[51] Int. Cl.$^6$ ............................................. G01N 3/08
[52] U.S. Cl. .............................. 73/794; 73/816; 73/821
[58] Field of Search .................. 73/794, 795, 38, 816, 73/821

[56] References Cited

U.S. PATENT DOCUMENTS

| | | | |
|---|---|---|---|
| 3,636,751 | 1/1972 | Pasini, III et al. | 73/38 |
| 3,906,782 | 9/1975 | Early et al. | 73/861 |
| 4,192,194 | 3/1980 | Holt | 73/794 |
| 4,579,003 | 4/1986 | Riley | 73/794 |
| 4,710,948 | 12/1987 | Withjack | 73/38 |
| 4,753,107 | 6/1988 | Reed et al. | 73/38 |
| 4,885,941 | 12/1989 | Vardoulakis et al. | 73/794 |
| 5,168,763 | 12/1992 | Stewart | 73/863.45 |
| 5,226,310 | 7/1993 | Steiger | 73/38 |

FOREIGN PATENT DOCUMENTS

| | | | |
|---|---|---|---|
| 0349422 | 1/1990 | European Pat. Off. | 73/795 |
| 1604686 | 12/1981 | United Kingdom . | |
| 1081348A | 3/1984 | U.S.S.R. . | |
| 1174823A | 8/1985 | U.S.S.R. . | |
| 1234625A1 | 5/1986 | U.S.S.R. . | |
| 1259035A1 | 9/1986 | U.S.S.R. . | |

OTHER PUBLICATIONS

Abstract–Test device of ground samples–has stamp and base made of central and sprung circular sections to ensure shear during compression, Gosstroi Cons Eng, Apr. 11, 1986, SU–054972.

*Primary Examiner*—Hezron E. Williams
*Assistant Examiner*—James M. Olsen
*Attorney, Agent, or Firm*—Bell, Seltzer, Park & Gibson

[57] ABSTRACT

The present invention relates to a test cell 1 suitable for use in applying directionally variable three dimensional stress fields to cylindrical test specimens 6 normally obtained by conventional coring techniques used for sample recovery. The test cell 1 comprises a cell body 2 having a barrel 4 extending therethrough for receiving a test specimen 6. The barrel 4 has an array 8 of elongate tubes 10 mounted side-by-side so as to line the inside wall 12 of the barrel. The tubes 10 have flexible side walls 14 and are formed and arranged for connection to a pressurized fluid supply 16. The test cell 1 also includes a control system 15 so that at least one tube 10a can be supplied with pressurized fluid at a different pressure to that in another tube 10b so as to provide an angularly variable radial pressure loading on the test specimen 6 mounted in the barrel 2.

12 Claims, 3 Drawing Sheets

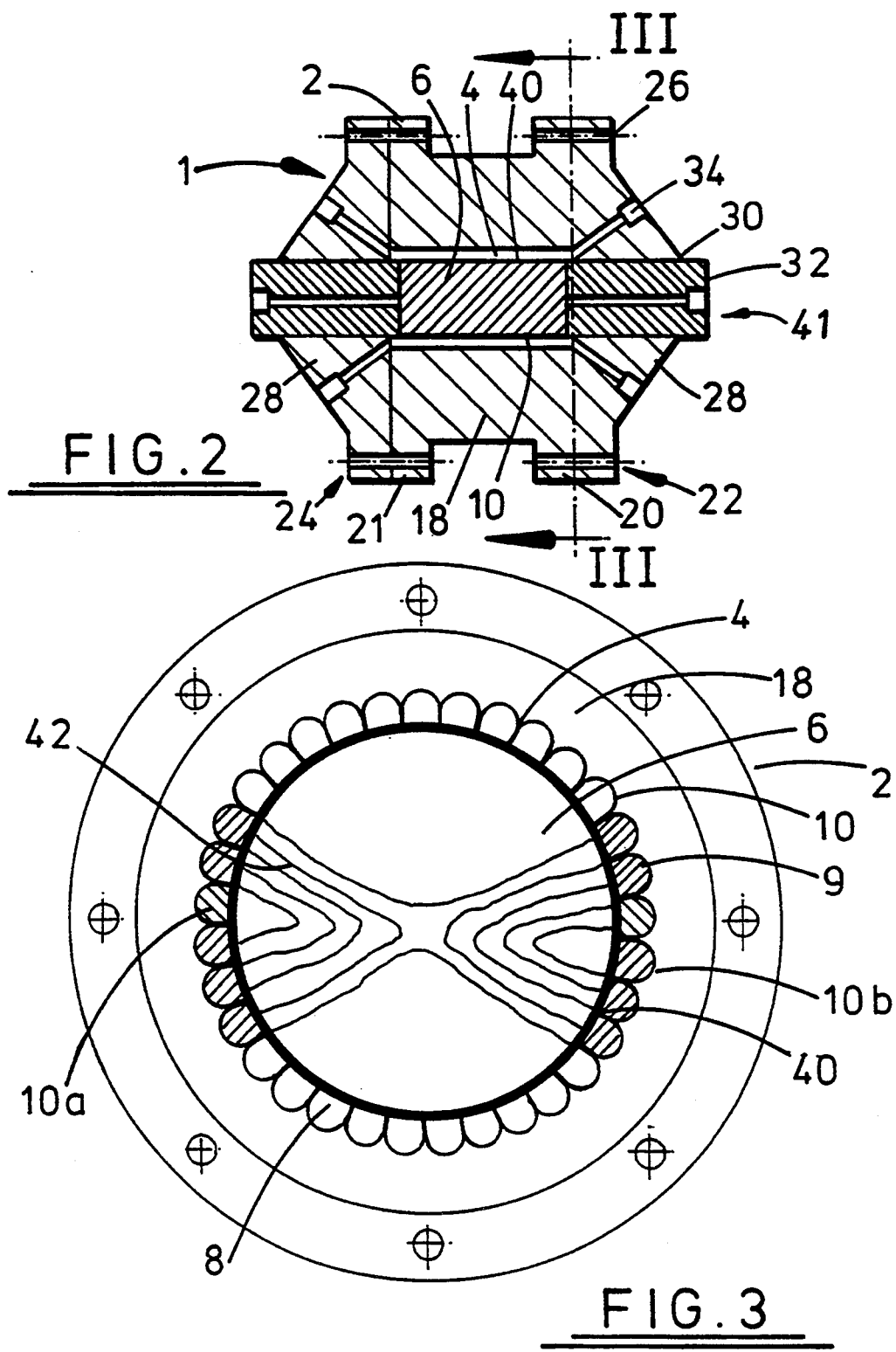

TEST CELL FOR APPLYING DIRECTIONALLY VARIABLE THREE DIMENSIONAL STRESS FIELDS TO A TEST SPECIMEN

The present invention relates to a test cell suitable for use in triaxially loading cylindrical material specimens especially rock samples but not exclusively.

Conventional test cells for triaxially loading test specimens apply a more or less uniform radial pressure or confining stress and an axial stress. A Hoek cell, for instance, applies axial stress on the two ends of a cylindrical specimen, while the radial stress is developed by pressurizing a hydraulic fluid such as oil, around the cylindrical surface of the specimen, in a test cell body in which the specimen is held. It will be seen that the radial stress is angularly uniform i.e. the same in all radial directions and the only variations possible in relation to differential stress loading are axial and radial (angularly uniform) relative to each other. Test data from the field has shown though that the radial stress, more usually referred to as the horizontal stress, is defined by two principal stresses and is asymmetrical. The horizontal stress applied by a Hoek cell is symmetrical and as such not suitable for use in for example well break-out, shear wave splitting and fracture propogation testing. In order that specimens may be tested with asymmetrical, horizontal stresses it has been necessary to prepare cubes of test material which much more accurately reflect the principal stresses encountered in an actual three dimensional situation. Such cuboid samples are however more difficult and expensive to prepare and test, furthermore cuboid samples are not generally preparable from the cylindrical test specimens (approx. 100 mm dia.) normally obtained by conventional coring techniques used for sample recovery e.g.in the petroleum industry where boreholes are sunk to depths of 3000 m.

It is an object of the present invention to avoid or minimize one or more of the above disadvantages.

The present invention provides a test cell suitable for use in applying directionally variable three dimensional stress fields to a polygonal—section test specimen which test cell comprises a cell body having a barrel extending therethrough formed and arranged for receiving a said test specimen therein, said barrel having an array of elongate tubes disposed in side-by-side relation lining the inside wall of said barrel, said tubes having flexible side walls and being formed and arranged for connection, in use, to a pressurized fluid supply means, said test cell including control means formed and arranged for supplying at least one said tube with pressurized fluid at a different pressure to that in another said tube thereby to provide an angularly variable radial pressure loading on a said test specimen mounted in said barrel.

It will be understood that the polygonal-section barrel may have any number of sides, including an infinite number of sides as in, for example, a cylindrical barrel which is generally preferred for strength and ease of manufacture of the test cell. In use of a cylindrical bore, said tubes may be mounted on said inside wall so as to be in side-by-side contact with each other. Preferably at least one of said inside wall and said multiplicity of tubes is provided with adhesion means formed and arranged to secure said tubes to said inside wall.

Preferably the inside wall of said barrel has a multiplicity of elongate grooves formed and arranged for locating said elongate tubes in side-by-side relation. Most preferably said grooves are more or less 'U'-shaped and said tubes have at least a more or less similarly shaped cross section formed and arranged to fit into said 'U'-shaped groove. Desirably said 'U'-shaped grooves are formed and arranged so as to permit tubes located therein to be in substantially direct contact with adjacent tubes.

It will be understood that the less space available for said tubes to expand into, when under pressure, the greater the pressure that may be applied over and above the normal rated unconfined capacity of the tube. Preferably the pressure differential attainable between adjacent tubes is at least 7000 kPa, advantageously at least 10,000 kPa. Desirably said test cell is capable of providing a said radial pressure of 50,000 kPa advantageously 70,000 kPa to the test specimen.

Preferably said tubes are generally 'D'-shaped in section with the 'flat' portion of said 'D'-shaped tube section disposed to face radially inwardly of the barrel for engagement with the radially outer surface of a said test specimen. Desirably the 'flat' portion of said 'D'-shaped tube is slightly concave so that the plurality of said tubes together when mounted inside said barrel define a substantially cylindrical bore for receiving a cylindrical said test specimen therein, though it will be appreciated that the flexibility of the tubes will normally provide a substantially even pressure to the specimen across the width of each tube when the tubes are pressurized.

It will of course be understood that tubes of any suitable section may be used, for instance rectangular section tubes, and that the inside wall of said barrel may be formed and arranged in any suitable manner to locate and/or mount said tubes.

Conveniently said cell body includes end caps formed and arranged to encapsulate a test specimen inside said test cell. Desirably said end caps are provided with ram means formed and arranged for applying the axial stress element of the three dimensional stress field to be applied to a said test specimen. Conveniently said axial stress element is applied and developed in a similar manner to that used in a Hoek cell.

Preferably said ram means on said end caps is formed and arranged for connection, in use, to the said pressurized fluid supply means. Preferably the test cell control means is formed and arranged for controlling the axial stress applied by said ram means. It will be appreciated though that a plurality of separate pressurized fluid supply means and/or a plurality of separate pressure control means such as valves may be used for controlling the pressures applied by the rams and tubes to different parts of the specimen.

The fluid in use in the supply means is preferably more or less non-compressible, for instance oil or water.

Preferably the test specimen has a resilient, for instance rubber liner place therearound, preferably 2-5 mm thick advantageously 3 mm thick, so as to prevent localized stress points on the surface of the specimen which are transmitted into the core of the specimen.

Desirably said liner is open-ended at both ends thereof. Furthermore said end caps are provided with drive means formed and arranged for progressively axially advancing said end caps relative to said ram means, so that in use of said test cell said end caps may be advanced axially of the liner thereby axially to compress said open-ended rubber liner so as to seal said end caps to said liner prior to the application of axial stress to the sample by said rams means. Advantageously the liner is formed and arranged so that upon axial compression said liner expands radially thereby filling any voids that may exist between said tubes, said barrel and said liner and said specimen contained therein, before pressurization of said tubes thereby reducing substantially the risk of tubes bursting when they are pressurized.

It will be appreciated that the thickness and compression characteristics of the liner may be varied considerably and the degree of axial compression applied to secure a desired level of sealing against the tubes also varied. The thickness and compression characteristics (specified by Young's Modulus and Poisson's Ratio) of the liner are generally selected in a combination which evenly distributes the pressures developed by the individual trapped tubes over the surface of the core under relatively low axial compression forces. One suitable combination is a 3 mm thickness of rubber with a Young's Modulus of 5 MPa and a Poisson's Ratio of 0.4. This combination was arrived at by constructing a finite element stress analysis computer model of a section through the rock core, liner, trapped tubes and cell. The Young's Modulus and Poisson's Ratio values were accepted for the rubber of the liner and the thickness varied until an even stress distribution was achieved.

When the end caps are sealed with said ends of said liner, the permeability of a said test specimen may be determined by passing pressurized fluid through the test specimen via apertures in said end caps.

The control means is conveniently provided with pressure and/or stress monitoring means formed and arranged for measuring the pressure in each of the tubes and for measuring the stress applied to a test specimen. Advantageously said sensing means may include strain gauges and the like which may be interfaced with computers for analysis by finite element analysis and other methods.

It will be understood that where an even number of tubes are mounted in the barrel the mathematical analysis of results therefrom is simplified compared to that with an odd number. Preferably from 4 to 100 tubes may be mounted inside a barrel, desirably from 8 to 50, advantageously from 20 to 30 tubes.

The test cell may also be provided with heating elements or the like so as to permit testing at elevated temperatures as may be found in actual field conditions.

Further preferred features and advantages of the present invention will appear from the following detailed description given by way of example of some preferred embodiments illustrated with reference to the accompanying drawings in which:

BRIEF DESCRIPTION OF DRAWINGS

FIG. 2 is a longitudinal cross section of the embodiment in FIG. 1;

FIG. 3 is an end view in the direction of line III—III of FIG. 2;

FIG. 1 shows a test cell of the invention, generally indicated by reference number 1. The test cell 1 comprises a cell body 2 having an elongate barrel portion 4. The barrel 4 is formed and arranged to receive a rock test specimen 6 inside thereof. The barrel 4 has an array 8 of tubes 10 mounted in grooves 9 in its inside wall 12 which are mounted side-by-side and circumferentially engage the specimen 6. Each of the tubes 10 has flexible side walls 14 and is connected via a control system 15 to a pressurized fluid supply 16 (See FIG. 4).

Figure 1:
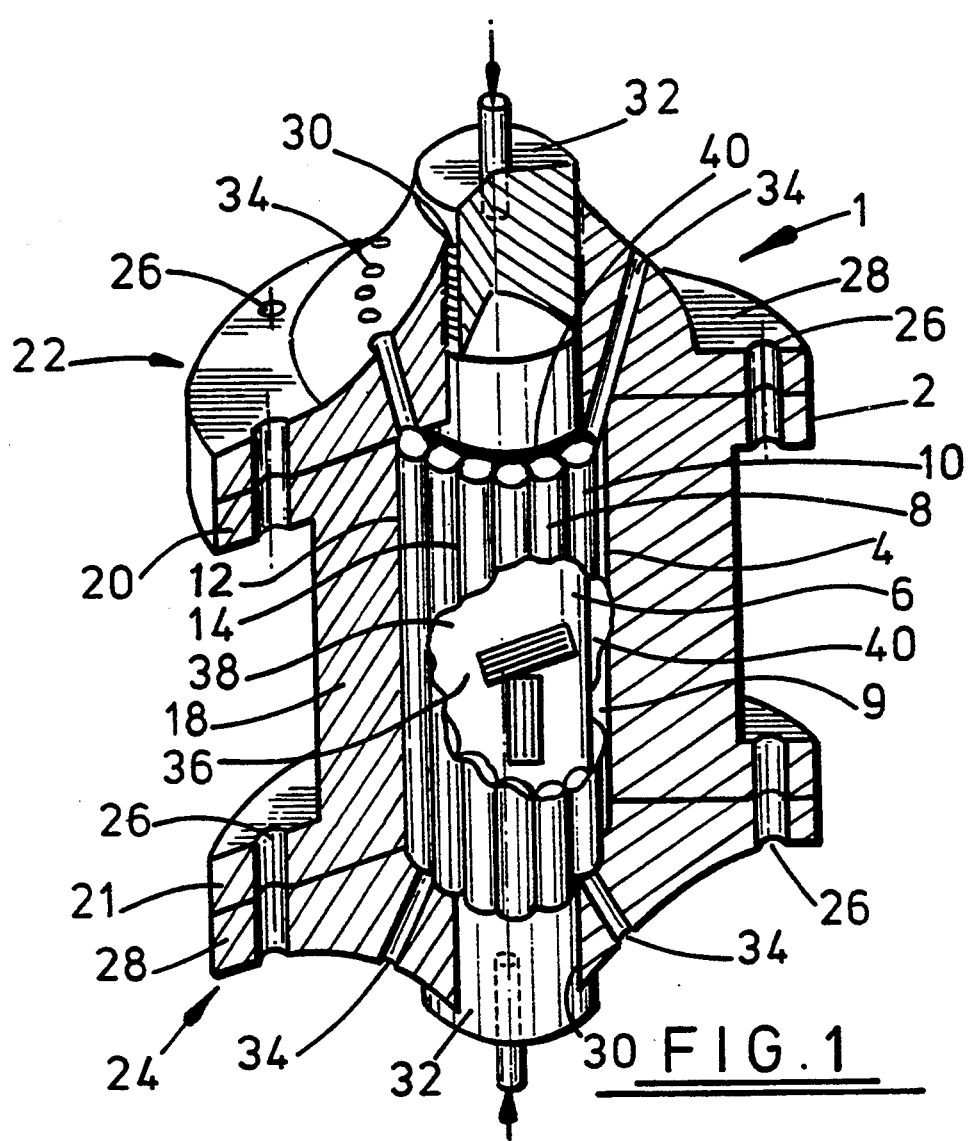
FIG. 1 is a partially sectioned orthogonal view of the main part of a test cell of the invention.

In more detail, the cell body 2 has a substantial central cylindrical part 18 with flanges 20, 21 on the top 22 and bottom 24 respectively thereof. Connected through eight holes 26 by bolts (not shown) to each respective flange 20, 21 is a machined end cover 28 which has a central bore 30 for receiving and holding axial stress rams 32. The end covers 28 have a plurality of holes 34 extending therethrough so that when the end cover 28 is bolted in place each hole 34 aligns and connects with a tube 10 of the array 8. Pressurized fluid is supplied via a control system 15, which will be described infra to the holes 34 so as to pressurize tubes 10 connected thereto at different pressures as required and thereby to apply angularly variable radial pressure to the test specimen 6.

The axial stress rams 32 apply axial or longitudinal stress to the test specimen 6, as required, and are also connected via the control system 15 to the pressurized fluid supply 16. Alternatively pressure may be applied to the test specimen 6 through platens of generally similar shape to the axial rams 32, the whole cell being mounted in a frame with one platen supported by the frame and the other engaged by a separate hydraulic press (not shown). The cutaway portion of FIG. 1 shows two strain gauges 36 mounted on the surface 38 of the test specimen 6 for measuring the applied pressure.

The test specimen 6 is mounted inside an open-ended tubular rubber liner 40 so as to prevent highly localized points of stress being transmitted through into the body of the specimen 6 and to distribute radial pressures more evenly whilst still maintaining the overall angular variation in loading from differently pressurized tubes.

FIG. 2 shows the main components of the test cell 1 described above with reference to FIG. 1 in longitudinal section.

The axial stress rams 32 have an axial aperture 41 passing therethrough, through which pressurized fluid (not shown) may be passed, By passing fluid through the test specimen 6 the permeability of the test specimen 6 may be calculated using known techniques.

FIG. 3 is an end view in the direction of line III—III of FIG. 2 with the central cylindrical part 18 of the cell body 2 and also shows an example of typical angularly variable stress distribution obtainable with the cell of the present invention. The barrel 4 of the body 2 has a plurality of 'U'-shaped grooves 9 in each of which is located a generally 'D'-shaped section tube 10. The test specimen 6 is mounted within its rubber liner 40 inside the array 8 of tubes 10. Two sets of tubes 10a, 10b (shaded) are supplied with pressurized fluid and exert radial pressure on the specimen 6. The contour lines 42 on the specimen 6 are representations of the stresses that may be developed in a test specimen 6 as a result of applying radial pressure through the set of tubes 10a, 10b.

It will be appreciated that a wide variety of angularly variable radial stress distributions may be obtained by supplying different tubes 10 or groups of tubes with pressurized fluid at different pressures so as to produce the often complex asymmetrical stress fields necessary for maximally useful permeability and microseismic experimentations.

Figure 4:
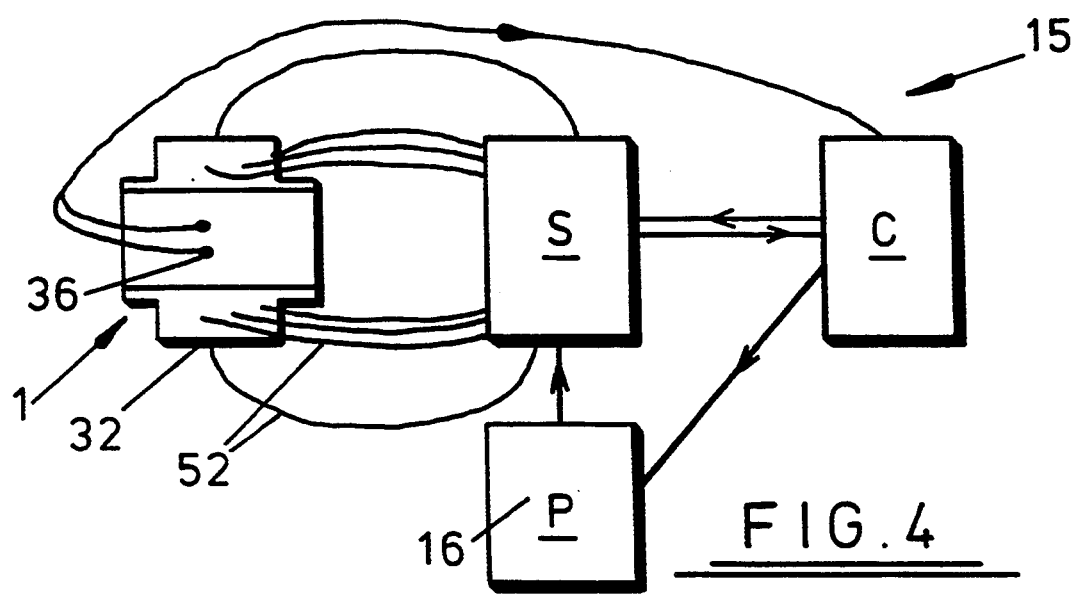
FIG. 4 is a schematic diagram of a cell of the invention showing the control means thereof.

FIG. 4 is a schematic diagram of the control system 15 of the embodiment described above with reference to FIG. 1. The test cell 1 is connected via supply pipes 52 to a hydraulic servo-mechanism S. A pump P pressurizes hydraulic oil and supplies 16 the servo-mechanism S both of which are controlled by a servo-controller C so as to pressurize the required tubes 10 and axial stress rams 32. The controller C is also provided with and connected to stress gauges 36 on the specimen 6, so as to provide feedback on the control by the servo-mechanism S.

Figure 5:
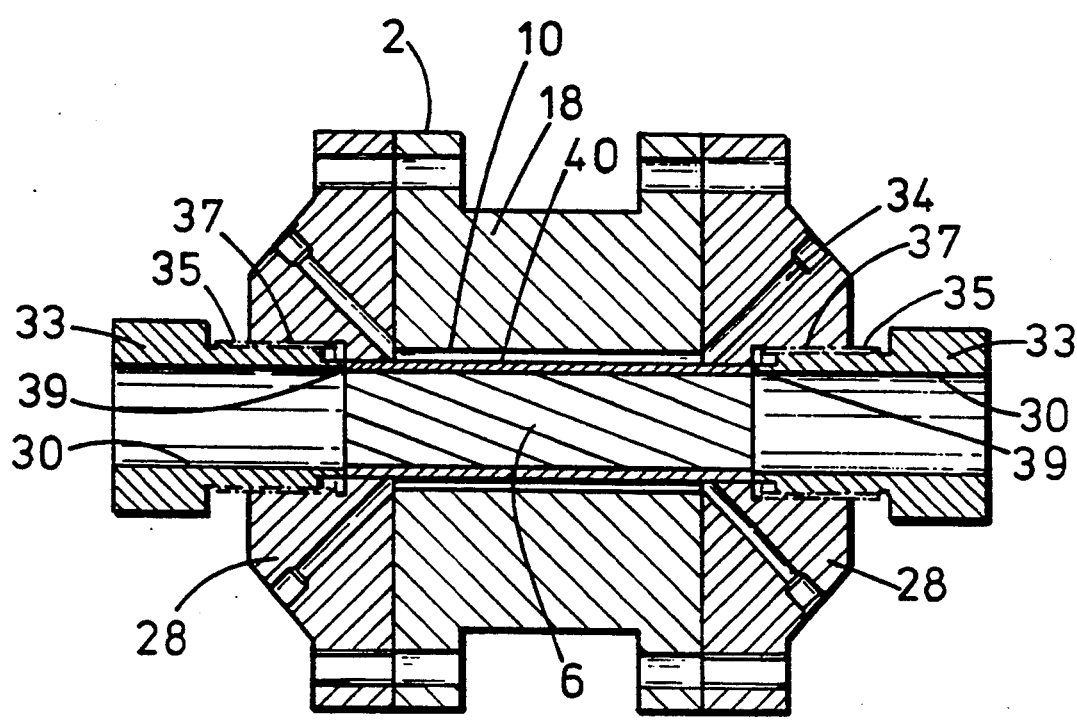
FIG. 5 is a longitudinal cross section of a second embodiment of a test cell of the invention.

FIG. 5 is a longitudinal cross section, generally similar to that of FIG. 2, of a second embodiment of the invention and will be described using like reference numbers. The axial stress rams 32 (not shown) are slidably mounted in the central bore 30 of stress ram supports 33. The stress ram supports 33 have a threaded outer portion 35 so that they may be screwthreadedly engaged in a threaded inner portion 37 of the end covers 28. The rubber liner 40 extends beyond the central cylindrical part 18 of the cell body 2 into the end covers 28 and the end faces thereof abuts the end face 39 of the stress ram supports 33. The stress ram supports 33 may be manually screwed into the cell body 2 so as to compress axially the rubber liner 40. The axial compression causes the rubber liner 40 to expand radially so as to fill any voids that may exist between the tubes 10, the liner 40 and the test specimen 6 contained in the test cell 2, especially any voids existing where the holes 34 leading to the tubes 10 meet the tubes 10 themselves, prior to the actuation of the axial stress rams, thereby minimizing the risk of rupture or other damage to the tubes at this relatively vulnerable part of the tubes when these are pressurized.

I claim:

1. A test cell suitable for use in applying directionally variable three dimensional stress fields to a polygonal—section test specimen which test cell comprises a cell body having a barrel extending therethrough formed and arranged for receiving a said test specimen therein, said barrel having an inside wall and a central axis, characterized in that said barrel has an array of elongate tubes disposed in side-by-side relation lining the inside wall of said barrel extending substantially axially along said barrel and substantially parallel to said central axis of the barrel, and, said tubes having flexible side walls and being formed and arranged for connection, in use, to a pressurized fluid supply means, said test cell including control means formed and arranged for supplying at least one said tube with pressurized fluid at a different pressure to that in another said tube thereby to provide an angularly variable radial pressure loading on a said test specimen mounted in said barrel.

2. A test cell as claimed in claim 1 characterized in that said barrel is in the form of a substantially cylindrical bore.

3. A test cell as claimed in claim 1 characterized in that said inside wall of said barrel has a multiplicity of elongate grooves extending substantially axially along said barrel and parallel to said central axis of the barrel, and said grooves being formed and arranged for receiving and locating respective ones of said elongate tubes.

4. A test cell as claimed in claim 3 characterized in that said grooves have a cross section generally similar to at least part of that of an elongate tube located therein.

5. A test cell as claimed in claim 3 characterized in that said grooves are generally 'U'-shaped, and are formed and arranged so as to permit tubes located therein to be in substantially direct contact with adjacent tubes, at portions thereof defining the barrel.

6. A test cell as claimed in claim 1 characterized in that each of said tubes is generally 'D'-shaped in section.

7. A test cell as claimed in claim 6 characterized in that the flat portion of said 'D'-shaped tube is slightly concave and is disposed to face radially inwardly of the barrel so that said array of tubes defines a substantially cylindrical bore for receiving a cylindrical test specimen therein.

8. A test cell as claimed in claim 1 characterized in that said cell body has end caps formed and arranged for applying and/or transmitting an axial stress loading to a said test specimen mounted in said barrel.

9. A test cell as claimed in claim 8 characterized in that said control means is further formed and arranged for supplying pressurized fluid to said end caps.

10. A test cell as claimed in claim 1 characterized in that said control means includes a plurality of pressure control valves for controlling the applied pressure.

11. A test cell as claimed in claim 1 characterized in that said control means is provided with pressure monitoring means formed and arranged for measuring the pressure and/or stress applied to a test specimen.

12. A test cell as claimed in claim 1 characterized in that said test cell has a resilient liner means formed and arranged for surrounding, in use, at least the radial periphery of said test specimen mounted in said barrel.

* * * * *